United States Patent [19]

Biller

[11] 4,270,010
[45] May 26, 1981

[54] HYDROQUINONE BY HYDROLYSIS OF P-AMINOPHENOL OR SALTS

[76] Inventor: Efim Biller, Hochstrasse 28, Zurich, Switzerland

[21] Appl. No.: 125,959

[22] Filed: Feb. 29, 1980

[30] Foreign Application Priority Data

Mar. 1, 1979 [CH] Switzerland .......................... 2045/79

[51] Int. Cl.³ ............................................ C07C 37/045
[52] U.S. Cl. .................................................. 568/767
[58] Field of Search ......................................... 568/767

[56] References Cited

U.S. PATENT DOCUMENTS

| | | | |
|---|---|---|---|
| 3,862,247 | 1/1975 | Greco | 568/767 |
| 3,932,538 | 1/1976 | Obara et al. | 568/767 |
| 3,935,283 | 1/1976 | Greco | 568/767 |
| 3,937,741 | 2/1976 | Greco | 568/767 |

Primary Examiner—Werren B. Lone

[57] ABSTRACT

Hydroquinone is made by heating an aqueous solution of p-aminophenol, or of a salt of p-aminophenol with an acid made by catalytic or electrolytic reduction of nitrobenzene, with an organic sulfonic acid, and extracting from the reaction mixture the hydroquinone by contact with a water-insoluble solvent. Residual organic sulfonic acid can be recovered from the hydroquinone-free reaction mixture and reused.

6 Claims, No Drawings

HYDROQUINONE BY HYDROLYSIS OF P-AMINOPHENOL OR SALTS

This invention relates to a method of preparing hydroquinone and pertains more specifically to a method of preparing hydroquinones through acid hydrolysis of p-aminophenol in aqueous solution containing organic sulfonic acids or containing the p-aminophenol salts of organic sulfonic acids from acid catalytic or electrolytic reduction of nitrobenzene.

Hydroquinone is made on a large scale by oxidation of aniline in sulfuric acid with manganese dioxide or sodium bichromate to quinone, and finally, reduction with iron or sulfur dioxide in water.

Greco U.S. Pat. No. 3,862,247 describes a procedure for hydrolysis of p-aminophenol with an aqueous solution of ammonium bisulfate, in which the ammonium sulfate formed by the hydrolysis is thermally converted, after evaporation of the water, into ammonium bisulfate which, after dilution with water and filtration of the resinous impurities is used again. The foregoing procedure possesses various disadvantages: (1) solid materials (resinous impurities) are formed during the hydrolysis; (2) the yield of hydroquinone is approximately 70%; (3) it is necessary to work with large volumes of water, since otherwise separation of ammonium bisulfate occurs; (4) in order to achieve good conversion, there must be used 2-3 moles of ammonium bisulfate for each mole of p-aminophenol; (5) in working with ammonium bisulfate, it is necessary to evaporate approximately 15-17 tons of water for each ton of hydroquinone.

Greco U.S. Pat. No. 3,935,283 describes hydrolysis of p-aminophenol (obtained by acid catalytic reduction of nitrobenzene) to hydroquinone with sulfuric acid and orthophosphoric acid. This process also has disadvantages: (1) the sulfuric acid leads to formation of by-products; (2) phosphoric acid must be used in large amounts and results in poor yields.

It is a feature of the present invention to provide a process for the production of hydroquinone through acid hydrolysis of p-aminophenol which does not display the specified disadvantages of other processes.

The foregoing result is achieved by carrying out the hydrolysis of p-aminophenol with aqueous organic sulfonic acids and by converting the ammonium salts of organic sulfonic acids formed thereby into ammonia and the free acids, either through contact with ion exchange resins or by contact with calcium or other water-insoluble salts, and separating the resulting aqueous solution of organic sulfonic acid for reuse in the process.

On feature of the present invention is a process for preparation of hydroquinone by acid hydrolysis of p-aminophenol characterized in that (a) p-aminophenol and/or p-aminophenol salts of acids obtained by catalytic or electrolytic reduction of nitrobenzene are hydrolyzed by heating, in one or more passes or steps, an aqueous solution containing 0.5-30% by weight, preferably 3-15%, of the p-aminophenol or p-aminophenol salts and containing 0.3-3, preferably 0.6-1.5 moles of organic sulfonic acid per mole of p-aminophenol, at temperatures of 190°-300° C., preferably 200°-265° C., for time periods of 0.01-10, preferably 0.1-3 hours for each pass, with separation of the hydroquinone formed after each pass by extraction with hydrophobic solvents, the extracts being worked up in conventional manner; and (b) the residual hydroquinone-free aqueous solution is freed wholly or partly from ammonia, either directly or after adjustment of pH to about 5 after treatment with a filter aid, by contact with an ion exchange resin or contact with insoluble salts of sulfuric acid, and the aqueous acid solution is reused in the process.

It has been shown that organic sulfonic acids display practically no side reactions during hydrolysis of p-aminophenol, which leads back to the conclusion that these are practically inert. As acids, there can be used all organic sulfonic acids which meet the following criteria:

(1). They possess stability under hydrolysis conditions. It is known that certain sulfonic acids tend to desulfonation at higher temperatures (above 150° C.). See Ullmanns, Encyclopedia of Technical Chemistry, 3rd Edition, Vol. 16, page 543.

(2). The p-aminophenol salt of the sulfonic acid displays sufficient solubility in water (Chambers et al., J. Org. Chem., Vol. 6, page 376 (1941).

Suitable are alkyl-, and aryl-sulfonic acids including benzene-, toluene-, and similar mono- and di-sulfonic acids, especially alkyl sulfonic acids containing 1 to 4 carbon atoms such as methane- and ethane-sulfonic acids, as well as trifluoromethane sulfonic acid.

Reaction time depends upon the temperature: at higher temperatures the reaction time for obtaining an equal weight of product is shortened.

The concentration of p-aminophenol in the solution can be, for example in the case of methane sulfonic acid, in the region of 0.5-30%, preferably 3-15% by weight of the solution.

The reaction temperature can vary in the region from 190°-300° C. since below about 190° C. the reaction is too slow, and above 300° C. too high a pressure of water vapor (above 105 ATM.) is required to maintain the liquid phase. Preferably the temperature range is from 200°-265° C. Hydrolysis times, depending upon temperatures, are in the region from 0.01 to 10 hours, preferably 0.1-3 hours. As hydrophobic solvents there can be employed practically all water-insoluble solvents which are sufficiently good solvents for hydroquinone, especially ethers, alcohols and esters. The hydroquinone can be extracted also at higher temperatures. In this case, there can be employed aromatic solvents as, for example, benzene and alkyl benzenes as well as diphenyl ether. The hydrolysis can take place in one or more steps or passes in order to provide maximum conversion of p-aminophenol to hydroquinone. The p-aminophenol can be made by any desired processes.

Of special significance is the possibility of producing the p-aminophenol salt of organic sulfonic acids in aqueous solutions directly from nitrobenzene through catalytic or electrolytic reduction and of using these directly for hydrolysis after separation of the unconverted nitrobenzene or catalyst and preparation of the necessary solution concentrations.

The by-products such as aniline and diaminodiphenylether which are produced during reduction do not interfere with the hydrolysis: aniline remains unchanged and the diaminodiphenylether is hydrolyzed to p-aminophenol.

Upon working up the hydrolyzate, the aniline can be liberated through adjustment of the pH to about 5 and can be obtained along with hydroquinone or separately according to the technique employed. Upon hydrolysis with sulfonic acids, there are formed, in contrast to known procedures, no insoluble materials except traces of oxidation products and polymers which cause discoloration of the hydrolysis solution. It was found quite surprisingly that these discoloring agents cannot be removed with ethers or ketones or esters. On the other hand, it is possible to remove the dissolved impurities by extraction with water-insoluble alcohols containing 4 or more carbon atoms, whereby there is obtained a pure aqueous solution of ammonium sulfonic acid salts as well as unconverted p-aminophenol sulfonate. It is advantageous to carry out the extraction of the hydroquinone with alkanols containing at least four carbon atoms, preferably 4–12 carbon atoms, whereby decoloration is simultaneously achieved. The removal of discoloration is of significance, expecially if the acids are to be regenerated over ion exchange resins for reuse.

The unconverted p-aminophenol can also be recovered in a conventional manner by adjusting the pH of the hydrolysis solution to pH 7-7.2 with a base (ammonia, sodium hydroxide, or other) before or after extraction of the hydroquinone. The p-aminophenol is then in free form and can be separated from the solution.

The fact that the calcium and barium salts of organic sulfonic acids are water-soluble has previously been used in technology for separating these acids from sulfuric acid.

Ammonia can be freed and separated by conversion of ammonium sulfonate into, for example, calcium sulfonate. Additionally, the calcium sulfonate is converted to calcium sulfate with sulfuric acid and separated by filtration. There are obtained aqueous solutions of sulfonic acids which can be returned to and reused in the hydrolysis. The process can be conducted in a continuous and/or a batch procedure.

Upon working up of the acid solutions with ion exchange resins, it is important that the solutions be very pure. It can be advantageous, before the ion exchange treatment, to treat the aqueous solutions with filter aids such as active charcoal, adsorbent clays and the like, which are, as far as possible, free from oxygen. Upon treatment with ion exchange reins, the p-aminophenol sulfonate remains unchanged as the salt, whereas the ammonia is, for the most part, bound; this is the result of the higher basisity of ammonia.

EXAMPLE 1

There were introduced into a 1½ liter glass lined container 109 g (1 mol) of p-aminophenol, 96 g (1 mol) of methane sulfonic acid, and 885 g of water (10% solution of p-aminophenol), and the mixture was allowed to react for 3 hours in an autoclave filled with water and heated to 240° C. The black colored solution which contained no solid materials was cooled and extracted with ether. There were obtained 72.0 g of crude hydroquinone, which after redistillation in vacuum gave 71.5 g of product shown to be pure by gas chromatography (gc). The aqueous solution was freed of dissolved ether and hydrolyzed by heating again for 3 hours at 240° C. The extraction yielded 25.0 g of crude product, which, after redistillation, yielded 24.5 g of pure (by gc) hydroquinone. By analysis, it was determined that there remained in the aqueous solution 12.5 g of p-aminophenol. The materials balance is as follows:

|  | First Hydrolysis | Second Hydrolysis |
|---|---|---|
| Conversion | 65.13% | 68.0% |
| Yield, pure hydroquinone | 99.3% | 99.0% |
| Overall materials balance: | | |
| Conversion | 88.53% | |
| Yield | 99.0% | |

The extracted black colored aqueous solution was extracted with n-amyl alcohol under nitrogen. The aqueous solution obtained was practically water white and could be converted verted into free acid by an ion exchange resin.

EXAMPLE 2

As a contrast with the example of U.S. Patent 3,862,247, the following test was conducted:

| Ingredient | U.S. Pat. No. 3,862,247 Amount | Present Invention Amount |
|---|---|---|
| p-Aminophenol | 32.7 g (0.3 mol) | 32.7 g (0.3 mol) |
| Ammonium bisulfate | 69.0 g (0.6 mol) | — |
| Methane sulfonic acid | — | 28.8 g (0.3 mol) |
| Water | 420 g | 460 g |
| Percent p-aminophenol based on total reaction mixture | 6.27 | 6.27 |

Both reaction mixtures were heated in glass lined containers for 3 hours at 240° C., and both reaction mixtures were worked up in the same way. The following results were obtained:

| | U.S. Pat. No. 3,862,247 | Present Invention |
|---|---|---|
| Solids | 1.4 g (4.25%) | None |
| Crude hydroquinone product | 27.0 g (81.8%) | 28.2 g (85%) |
| Pure hydroquinone | 24.0 g (72.7%) | 28.0 g (84.8%) |
| Residue | 2.0 g (6.1%) | 0.2 g (0.2%) |
| Water evaporated per kg hydroquinone | 17.320 kg | |

What is claimed is:

1. Process of making hydroquinone from p-aminophenol or from salts of p-aminophenol with acids made by catalytic or electrolytic reduction of nitrobenzene, which process comprises
    heating at a temperature of 190°–300° C. an aqueous solution containing 0.5 to 30% by weight of said p-aminophenol or p-aminophenol salt and containing 0.3–3 moles of organic sulfonic acid per mole of said p-aminophenol or p-aminophenol salt to form a reaction mixture containing hydroquinone, and
    extracting said hydroquinone from said reaction mixture by contacting said mixture with a water-insoluble solvent for said hydroquinone to leave a hydroquinone-free aqueous mixture.

2. Process as claimed in claim 1 which comprises contacting said hydroquinone-free aqueous mixture with an ion-exchange resin or with a water-insoluble salt of sulfuric acid to liberate free organic sulfonic acid and to free the aqueous mixture at least in part from ammonia, and
    reusing the resulting aqueous solution of organic sulfonic acid in said process.

3. Process as claimed in claim 1 comprising reheating said hydroquinone free aqueous mixture at 190°–300° C.

to form a second reaction mixture containing additional hydroquinone, and extracting said additional hydroquinone from said second reaction mixture by contacting it with a water-insoluble solvent for hydroquinone.

4. Processs as claimed in claims 1, 2 or 3 in which said water-insoluble solvent is an alkanol containing at least 4 carbon atoms.

5. Process as claimed in claims 1, 2 or 3 in which the organic sulfonic acid is an alkyl sulfonic acid containing 1 to 4 carbon atoms.

6. Process as claimed in claims 1, 2 or 3 in which the organic sulfonic acid is trifluoromethane sulfonic acid.

* * * * *